(12) United States Patent
Borch et al.

(10) Patent No.: US 10,228,308 B2
(45) Date of Patent: *Mar. 12, 2019

(54) METHOD OF TRANSFERRING BEADS

(71) Applicant: SpinChip Diagnostics AS, Oslo (NO)

(72) Inventors: Stig Morten Borch, Oslo (NO); Torgeir Hamsund, Oslo (NO); Jostein Geir Holtlund, Høvik (NO); Anja Gulliksen, Oslo (NO)

(73) Assignee: SpinChip Diagnostics AS, Oslo (NO)

( * ) Notice: Subject to any disclaimer, the term of this patent is extended or adjusted under 35 U.S.C. 154(b) by 126 days.

This patent is subject to a terminal disclaimer.

(21) Appl. No.: 15/319,717

(22) PCT Filed: Jun. 19, 2015

(86) PCT No.: PCT/EP2015/063824
§ 371 (c)(1),
(2) Date: Dec. 16, 2016

(87) PCT Pub. No.: WO2015/193478
PCT Pub. Date: Dec. 23, 2015

(65) Prior Publication Data
US 2017/0138939 A1 May 18, 2017

(30) Foreign Application Priority Data
Jun. 19, 2014 (NO) .................................. 20140777

(51) Int. Cl.
*G01N 1/10* (2006.01)
*G01N 33/543* (2006.01)
(Continued)

(52) U.S. Cl.
CPC .......... *G01N 1/10* (2013.01); *B01L 3/502753* (2013.01); *B01L 3/502761* (2013.01);
(Continued)

(58) Field of Classification Search
CPC ....... G01N 33/54313; G01N 33/54333; G01N 33/54366; G01N 1/10; G01N 2001/1006;
(Continued)

(56) References Cited

U.S. PATENT DOCUMENTS 8,191,715 B2 * 6/2012 Cho .................. B01L 3/502738
210/360.1
9,162,227 B2 * 10/2015 Borch ............... B01L 3/502738
(Continued)

FOREIGN PATENT DOCUMENTS

EP 1 994 987 11/2008
EP 2 810 717 12/2014
(Continued)

OTHER PUBLICATIONS

International Search Report and Written Opinion dated Jul. 30, 2015, directed to International Application No. PCT/EP2015/063811, 11 pages.

(Continued)

*Primary Examiner* — Maureen Wallenhorst
(74) *Attorney, Agent, or Firm* — Morrison & Foerster LLP

(57) ABSTRACT

A method for transferring beads in a fluidic chip having an internal fluid circuit through which various reactants, including beads, may be moved by use of centrifugal force includes providing beads having a density equal to, or lower than, m1 in a section of the fluid circuit, where the section includes at least a first outlet. The method includes providing a first liquid medium having a density d2 to the section, such that d2>m1, and applying a centrifugal force such that the beads migrate in an opposite direction of the centrifugal force.

7 Claims, 7 Drawing Sheets

(51) Int. Cl.
*B01L 3/00* (2006.01)
*B03D 3/00* (2006.01)
*G01N 35/04* (2006.01)

(52) U.S. Cl.
CPC ......... *B03D 3/00* (2013.01); *G01N 33/54313* (2013.01); *G01N 33/54333* (2013.01); *G01N 33/54366* (2013.01); *B01L 2200/0647* (2013.01); *B01L 2200/10* (2013.01); *B01L 2400/0409* (2013.01); *B01L 2400/0487* (2013.01); *G01N 2001/1006* (2013.01); *G01N 2035/0449* (2013.01)

(58) Field of Classification Search
CPC ..... G01N 2035/0449; B01L 2200/0647; B01L 2200/10; B01L 2400/0409; B01L 2400/0487; B01L 3/502753; B01L 3/502761; B03D 3/00
USPC ............ 436/43, 45, 63, 174, 177, 178, 180; 422/72, 501, 502, 503, 506, 533; 435/7.94
See application file for complete search history.

(56) References Cited

U.S. PATENT DOCUMENTS

| | | | |
|---|---|---|---|
| 9,927,328 B2* | 3/2018 | Borch | G01N 1/10 |
| 2009/0104077 A1 | 4/2009 | Momose | |
| 2013/0313483 A1* | 11/2013 | Mace | B03B 5/28 252/408.1 |

FOREIGN PATENT DOCUMENTS

| | | |
|---|---|---|
| WO | WO-01/38865 | 5/2001 |
| WO | WO-2011/081530 | 7/2011 |
| WO | WO-2013/138763 | 9/2013 |
| WO | WO-2015/193478 | 12/2015 |

OTHER PUBLICATIONS

International Search Report and Written Opinion dated Sep. 28, 2015, directed to International Application No. PCT/EP2015/063817, 11 pages.

International Search Report and Written Opinion dated Jul. 30, 2015, directed to International Application No. PCT/EP2015/063824, 10 pages.

International Preliminary Report on Patentability dated Jul. 7, 2016, directed to International Application No. PCT/EP2015/063817, 6 pages.

International Preliminary Report on Patentability dated May 19, 2016, directed to International Application No. PCT/EP2015/063824, 7 pages.

Norwegian Search Report dated Jan. 19, 2015, directed to NO Application No. 20140777, 3 pages.

Lee, W., et al. (Jan. 2013). "A centrifugally actuated point-of-care testing system for the surface acoustic wave immunosensing of cardiac troponin I," *The Analyst* 138(9): 2558-2566.

Arosio, P., et al. (Dec. 2013). "Density-Gradient-Free Microfluidic Centrifugation for Analytical and Preparation Separation of Nanoparticles," *Nano Letters* 14(5): 2365-2371.

Genung, R. K., et al. (May 1978) "Interaction of Antibody with Antigen Immobilized on Polystyrene Latex Beads: Characterization by Density Gradient Centrifugation," *Analytical Biochemistry* 91(2): 651-662.

* cited by examiner

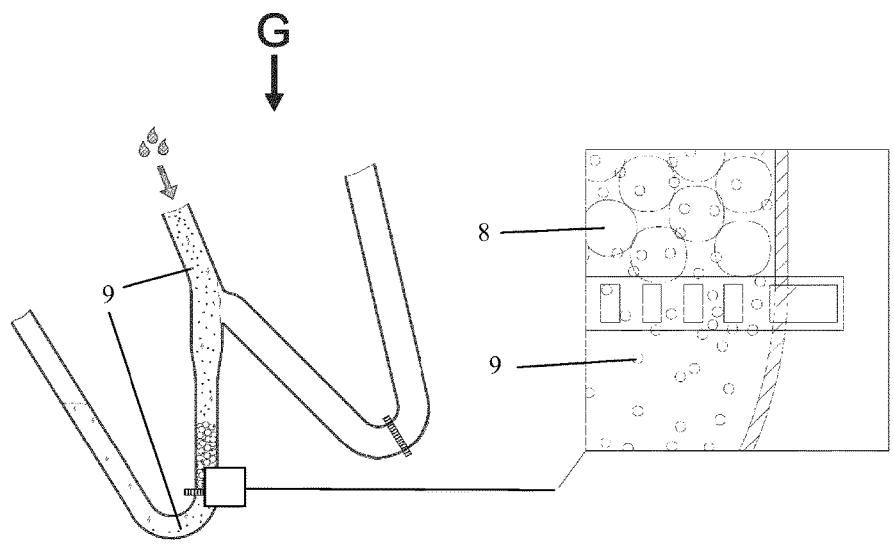
Fig. 1d
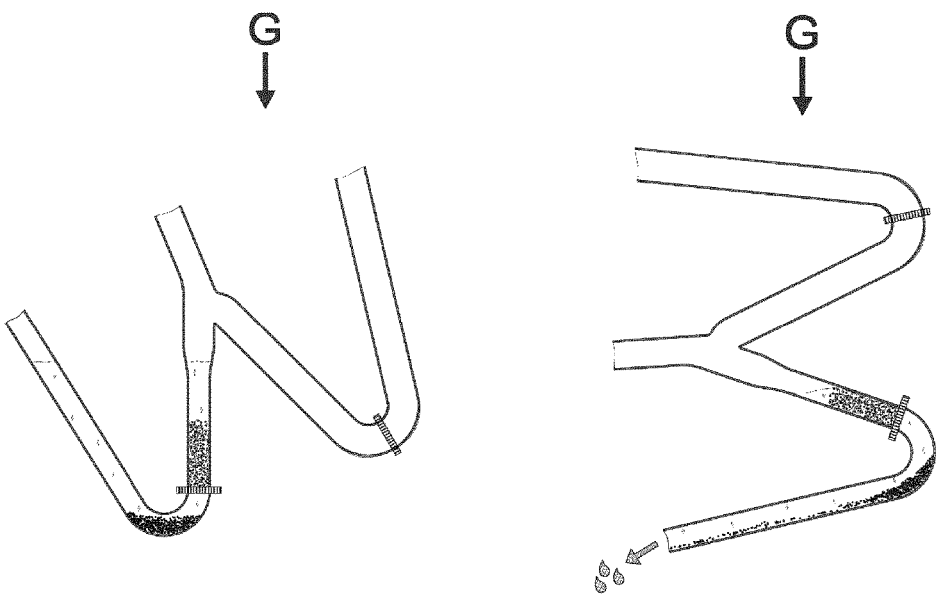
Fig. 1e
Fig. 1f

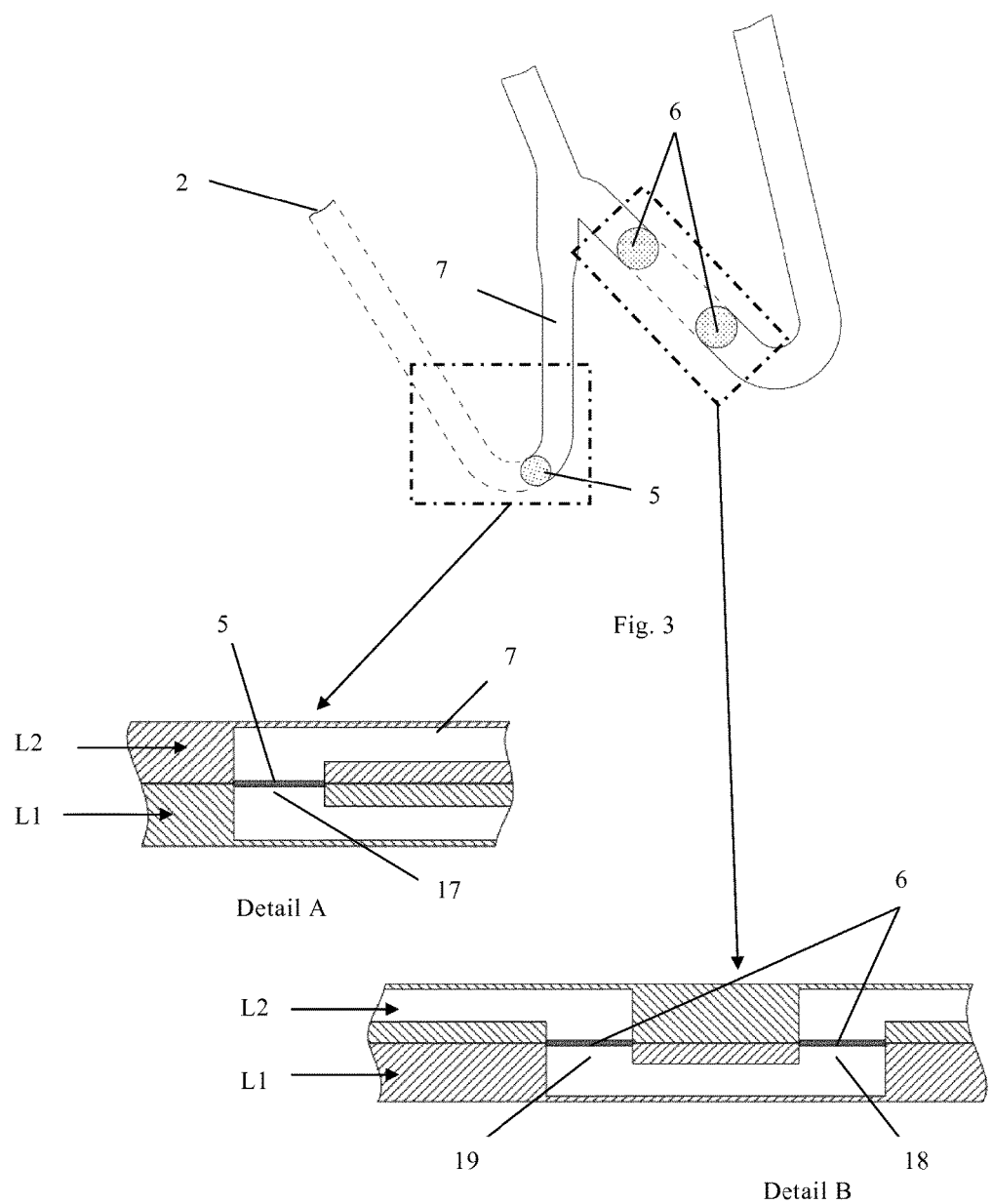

METHOD OF TRANSFERRING BEADS

CROSS-REFERENCE TO RELATED APPLICATIONS

This application is a U.S. National Stage patent application of International Patent Application No. PCT/EP2015/063824, filed Jun. 19, 2015, which claims priority to Norwegian Application No. 20140777, filed Jun. 19, 2014, each of which is hereby incorporated by reference in the present disclosure in its entirety.

FIELD OF THE INVENTION

The present invention relates to the field of fluidic devices utilizing centrifugal forces for processing and moving liquids and more specifically concerns a method of transferring beads in such devices. A preferred field of use is in an analytical method performing an analysis of a compound present in a sample. The transfer method is advantageously used when an analytical device (lab-on-a-chip), in which fluidic or microfluidic processing occurs, is used in connection with a centrifuge, and preferably a centrifuge providing means for changing the orientation of the analytical device relative to the direction of the applied centrifugal force.

BACKGROUND OF THE INVENTION

The method of transferring beads according to the present invention was conceived during research concerning analytical methods suitable for use in fluidic or microfluidic chips or cartridges. To better understand the advantages of the present invention, such analytical methods are described in detail below.

A common method of analyzing for a certain substance or analyte involves the use of a solid phase which will selectively bind to the target substance or analyte which typically is a biomarker. In some assays a solid phase may on its surface carry and display specific capturing molecules which will specifically bind the biomarker. In order to detect and quantify said biomarker, the solid phase-biomarker complex may also react with another set of biomarker specific binding molecules attached to one or more tracer substance(s) forming a solid phase-biomarker-tracer complex(es). In other assays, such as competitive immunoassays, the biomarker in the sample will compete with a defined amount of biomarker carrying the tracer substance in the binding to the solid phase. There are numerous ways of arranging and using the involved specific binders and target analytes, including various types of solid phase materials and tracer substances.

In many analytical systems, the solid phase comprises a fixed embodiment such as the walls of cavities (microtiter plate wells or microchannels and microcavities) or fixed structures, such as pillars or porous membranes, on which the capturing molecules, for instance antibodies, being complementary to the biomarker, for instance an antigen, are attached. Lateral or transversal flow, of the sample containing the target biomarker, through porous membranes is a preferred solid phase concept when it comes to binding of the target biomarker. This is due to the fact that the surface to volume ratio is very large in these membranes allowing for a large excess of the capturing molecules, e.g. antibodies, and hence very efficient binding of the target biomarker. However, these membranes are difficult to wash particularly when the tracer is a nanoparticle or agglomerates thereof. This difficulty is caused by unspecific binding or entrapment of the tracer substance in pocket-like structures within the membrane.

In other analytical systems, the solid phase may advantageously be spherically shaped nano- or microsized particles made in polymeric materials exposing a large surface area.

The tracer can be any type of substance that may be detected and measured by either optical, chemical, electrical, magnetic, radioactive means or combinations thereof. Further, the tracer substance may also be formulated as or associated with a particle. Such particles frequently used and detected by optical means includes metal colloids (gold, silver, iron and others), quantum dots, polymer (latex) particles containing or carrying dyes or fluorochromes, polymer, silica or other particles carrying signal generating molecules including enzymes or inorganic crystals such as upconversion nanoparticles (UCNPs). The particles used as tracer substances or carriers are usually in the nanometer range typically between 2 nm to 200 nm, but larger particles up to 100 µm may be used in some settings. The biomarker specific molecules attached respectively to the solid phase and the tracer substances may for example be antibodies that will specifically bind to the target biomarker, which is then referred to as the antigen. Frequently used alternatives to antibodies includes nucleic acid probes, avidin/streptavidin, lectins and aptamers as well as any (bio)receptor that will recognize and specifically bind to defined molecular structures of the ligand (i.e. the analyte or part of the analyte). Actually, a major part of all proteins within nature interact more or less specifically with some ligand which may be a defined structure of a large molecule or small molecules. Usually, the more specific and the higher the affinity the binding is the more suited the receptor ligand system is for designing analytical assays. To quantify the solid phase-biomarker-tracer substance complex, (in the following also referred to as a quantifiable bead complex) the tracer substance must display certain properties allowing identification and measurement. Optical readout systems are often particularly convenient as the detector may be placed outside the assaying device. Properties of optical tracer substances include light absorption, light scattering as measured by transmittance or reflectance as well as light diffraction and luminescent phenomena like chemoluminescence, fluorescence, upconversion phosphorescence and others including combinations thereof. The phenomena are typically referred when measuring colors, luminescence such as fluorescence and phosphorescence, diffraction, plasmon effects and others.

In most heterogeneous types of analytical assays the target biomarkers are first allowed to react with the solid phase and tracer substance in excess. Then the tracer substance not specifically bound to the solid phase is removed by washing.

To have the target biomarker bind to the solid phase and the tracer substance, respectively, they will have to interact directly. With high affinity binders, the more often the reactants, i.e. the biomarker, solid phase and tracer substance, interact or collide the faster the binding reaction. Thus, to obtain a fast assay one should establish reaction conditions with very high local concentration of the high affinity and specific binding substances. To establish such conditions, the solid phase should expose a large surface area crowded with specific, high affinity receptor molecules. Similarly the tracer substance carrying the second set of specific and high affinity receptor molecules should be present in high concentrations. Suspensions of nano- and microparticles expose large surface to volume ratios, similar to porous structures such as porous membranes. Fluidic movements that will further facilitate collisions between the reactants involved should be applied. Such movements may be obtained by moderate heating and stirring, but more preferably by making the sample and the reagents, including the tracer substance in case of non-competitive assays, pass/flow through the solid phase. Liquids flowing through solid phase materials like porous membranes, micro-channels, micro-pillar structures or stacked particles are hence preferred in designing efficient binding assays.

The same consideration as discussed in the previous paragraph applies equally well in a competitive heterogeneous assay. In such assays the solid phase expose a large surface area crowded with bound and labeled biomarkers.

Spherical micro- and nanoparticles are often preferred as solid phase materials for several reasons:

Particles have a very large surface to volume ratio.

Particles are efficiently functionalized in batch and can hence be mixed to form homogenous suspensions.

Particle suspensions can be dispensed in aliquots that may be used directly in liquids form or be formulated as dried aliquots such as tablets or freeze dried spheres.

Particles may be loaded with or made from materials that add distinct features to the particles. This includes distinct optical features like light absorption, light scattering, light emittance (luminescence) and more, as well as magnetism, radioactivity, catalytic/enzymatic, electrochemical, and other measurable features.

Particles may be transported within microfluidic systems when in suspension.

Particles may be efficiently mixed with the sample in solution.

Particles in suspensions may be separated from the solution by gravity, centrifugation, filtration, magnetic force (magnetic particles) or electric force or combinations thereof.

Particles may sediment, stay in suspension or float depending upon their density relative to the medium in which they are dispersed.

Particles can be made monodisperse and completely spherical both being porous or with a smooth solid surface without pores.

Particles may be packed or stacked in a variety of containers including columns.

Particles may be opaque (colored) or substantially transparent allowing compatibility and use in a variety of optically based measuring systems.

When compact monodisperse particles are stacked onto a filter, like in columns, they may form a porous lattice structure with regular and defined spacing. Liquids may flow in a controlled and reproducible manner through such columns.

The most efficient way to make an analyte, and optionally a tracer substance in case of non-competitive assays, interact with immobilized capturing molecules, attached to the surface of solid phase particles, is to pack the particles onto a filter or slit in the form of a column and allow a solution containing the analyte, and/or reagents such as a tracer substance, pass through the column of particles. This can be done sequentially and in repetitive steps or by applying a mixture of both the analyte(s) and tracer substance(s) and letting them pass in one step.

After the reaction or binding step(s), the solution is separated from the solid phase and the solid phase washed to remove remaining excess tracer substances, labeled unbound analyte (as in competitive assays) etc., to obtain a consistent and accurate analysis.

The use of bead columns to obtain an efficient interaction between the beads and various tracer substances and/or analytes is known from analytical methods using microfluidic chips.

US 2009/0104077A1 discloses a method for performing an ELISA-assay (Enzyme Linked ImmunoSorbent Assay) in a microfluidic chip. The disclosed microfluidic chip has a fluid circuit which comprises a column structure filled with beads acting as the solid phase. An ELISA-type reaction is performed on the beads in the column structure by first forming a bead-biomarker-enzyme-labeled antibody complex. The excess of enzyme-labeled antibody is then removed by letting a washing liquid flow through the column by application of a centrifugal force. An important feature of said method is the ability to circulate the same washing fluid multiple times through the column to obtain an improved washing step. After the cleaning or washing step, a color-generating substrate is applied to the enzyme-labeled complexes and the generated color may for instance be measured at the column structure. At least one end of the column structure ends in a restricted passage preventing the solid phase beads from passing out of the column.

WO 2011/081530 A1 discloses a processing cartridge (i.e. a fluidic or microfluidic chip) for analyzing a test sample, for instance a biological sample such as whole blood. The cartridge is adapted for use in a centrifuge analyzing instrument. The cartridge may comprise particular fluid circuit elements described as traps. Such an element is used to form a column of solid phase particles (beads), wherein the particles may be retained while a fluid is passed through the column. By appropriately changing the direction of an applied centrifugal force relative to the cartridge, a fluid, containing various reactants (e.g. biomarker and tracer substance) which react with the solid phase particles, is passed through the column repeatedly. The design of the traps avoids the use of a filter, or narrow fluid path, to obtain a column of particles or beads. Removal of excess reagents is obtained by repeated washings of the particles. The description of the traps and their use, as well as the concept of microfluidic chips having a fluid circuit through which circuit a sample comprising an analyte, and various optional reagents and solvents, may be moved by the use of centrifugal force, are hereby incorporated by reference.

In other assay systems ferromagnetic particles are used as the solid phase to facilitate the washing or separation steps. A magnet is then temporary used to pull the particles to one wall of a reaction container and withholding them during separation from the liquid. When the reaction container is moved away from the magnet, the particles are free to be re-suspended in solution. However, the magnetic particles are optically dense due to their content of ferromagnetic materials and they will hence significantly quench the optical readout. For this reason ferromagnetic particles are not suited for use in combination with tracer labels that are being bound to the particles through the assay.

In the technical field of sample analysis, such as analysis of biomarkers, both the use of a stationary and a mobile solid phase in assays are known. The present invention relates inter alia to the use of such assays in microfluidic chips (i.e. processing cartridges) having a fluid circuit through which circuit a sample comprising an analyte, and various optional reagents and solvents, may be moved by the use of centrifugal force. Such microfluidic chips are disclosed in for instance Schultz et al. Clin. Chem. 1985, 31, 1457, U.S. Pat.

No. 488,763, and the above-mentioned patent applications US 2009/0104077 A1 and WO 2011/081530 A1.

In heterogeneous type analytical assays, efficient and reproducible separation (washing) of the excess unbound tracer substance from the tracer substance being bound to the solid phase is essential for reliable analytical results. Efficient washing is particularly important in high sensitivity analyses.

A solid phase having a porous structure, such as porous membranes, is more difficult to wash efficiently than solid phases having smooth surfaces like those available on well walls, micro-pillars or spherical particles. However, a solid phase comprising spherical particles (e.g. beads) closely packed into a column experiences some of the same difficulties as those encountered in porous membranes regarding efficient and reproducible washing. The close interaction of the beads in a packed column provides a temporary porous structure (i.e. due to voids formed in between the beads) within which unbound tracer substances (i.e. tracer substance not bonded to the solid phase) is easily captured in a non-specific manner. In the prior art, such columns are washed by passing a washing liquid through the column. However, even if such a washing is repeated multiple times (ref. the disclosure of US 2009/0104077A1), at least some of the unbound tracer substance will remain captured in the porous structure and subsequently have a negative impact on the reproducibility and sensitivity of the assay.

A common feature of the prior art analytical methods performed in fluidic or microfluidic chips, wherein an applied centrifugal force is used for optionally moving beads or solid phase particles through an internal fluid circuit, is that said beads, or solid phase particles, are moved in the same direction as the centrifugal force. This feature puts limitations and constraints on the possible designs of the internal fluid circuit.

The present invention relates to a method of transferring beads, or solid phase particles, in a fluidic or microfluidic chip comprising an internal fluid circuit which avoids or mitigates at least some of the disadvantages of the prior art.

SUMMARY OF THE INVENTION

The present invention relates to a method of transferring beads, or solid phase particles, in a fluidic or microfluidic chip comprising an internal fluid circuit which avoids or mitigates at least some of the disadvantages of the prior art. The method is defined by the appended claims, and in the following:

In one embodiment, the present invention provides a method of transferring beads in a fluidic chip comprising an internal fluid circuit through which various reactants, in which at least one of the reactants are beads, may be moved by use of centrifugal force, the method comprises the steps of:
  providing beads having a density equal to, or lower than, m1 in a section of the fluid circuit comprising at least a first outlet;
  providing a first liquid medium to the section of the fluid circuit, the liquid medium having a density d2, such that d2>m1; and
  applying a centrifugal force such that the beads migrate in the opposite direction of the centrifugal force.

In one embodiment of the method of transferring beads in a fluidic chip, the beads migrate towards the first outlet.

In one embodiment of the method of transferring beads in a fluidic chip, the method comprises the step of:
  transferring the beads out of the section by changing the direction of the centrifugal force, preferably such that the beads are decanted through the first outlet.

In an embodiment of the method of transferring beads in a fluidic chip, the fluidic chip is arranged in a centrifuge capable of providing the centrifugal force.

In a preferred embodiment of the method of transferring beads in a fluidic chip, the fluidic chip is a microfluidic chip.

In another preferred embodiment of the method of transferring beads in a fluidic chip, the direction of the centrifugal force relative to the internal fluid circuit may be varied in at least two separate directions.

In a further embodiment of the method of transferring beads in a fluidic chip, the reactants includes a sample containing one or more analytes.

In all embodiments, the fluidic chip may advantageously be a microfluidic chip. However, in some cases it is envisioned that a fluidic chip for volumes in the ml-range may be preferred.

The first liquid medium may be provided as is, or the required density may be obtained by adding a high or low density liquid to, or dissolving a high density solid in, a liquid medium already present in the section. In other words, when a liquid medium of a certain density is provided, it does not necessarily require the addition of the liquid medium to the section, but it may be provided by altering the density of a liquid medium already present in the section.

In the present application, the term "fluidic chip" is intended to encompass any type of chip or cartridge comprising an internal fluid circuit through which various reactants, including beads and a sample containing at least one analyte, may be moved by use of centrifugal force.

BRIEF DESCRIPTION OF THE DRAWINGS

FIGS. 1a-1k are schematic drawings showing the steps used in an analytical method suitable for use with the present invention.

FIG. 3 is a schematic drawing showing further details of a microfluidic circuit suitable for use in the method according to the invention.

DETAILED DESCRIPTION OF THE INVENTION

Figure 1A:
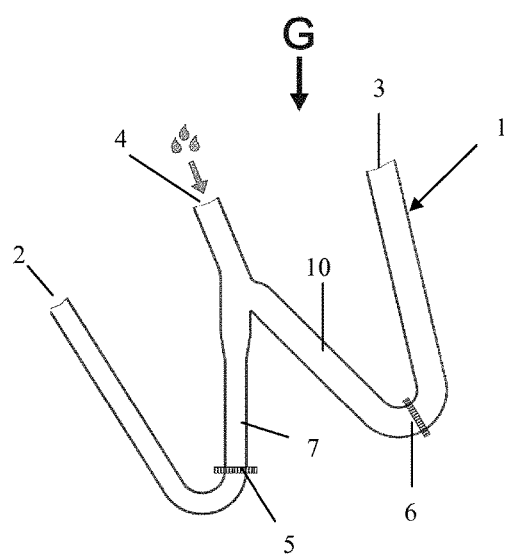

The term «analyte» is in the context of the present invention to be understood to cover any compound that may be determined, quantitatively or qualitatively in the method according to the present invention. In particular the term "analyte" is intended to encompass any compound that can be used as an indicator of a particular disease state or some other physiological state of an organism, preferably the human body (i.e. a biomarker). The biomarker may for instance be a biomarker for Anemia, such as Erythropoietin (EPO) Ferritin, Soluble Transferrin Receptor (sTrR), Folic Acid (folates), Transferrin, Hemoglobin, Vitamin B12, a biomarker for Bone disease such as Alkaline Phosphatase (ALP), Osteocalcin, Parathyroid Hormone (PTH), Bone Specific Alkaline Phosphatase (BSAP), Vitamin D, 1,25 Dihydroxy, C-Terminal Type I Collagen Telopeptide (CTx), Vitamin D, 25 Hydroxy, N-terminal Type I Collagen Telopeptide (NTx), a biomarker for a Cardiac disease such as Apolipoprotein E (Apo E), Brain Natriuretic Peptide (BNP), LDH, CK, CKMB, Pro-B-type Natriuretic Peptide (Pro-BNP), C-Reactive Protein (CRP), Troponin I, Trponin T, CRPhs (ultrasensitive), a biomarker for Diabetes such as C-Peptide, HbA1c, IA-2 Antibody, Insulin, Fructosamine, Insulin Growth Factor (IGF-1), Glucagon, Microalbumin, Glucose, Proinsulin, Antibody, a biomarker related to Endocrinology such as Alpha-Foetoprotein, Growth Hormone, Adrenal Corticotrophic Hormone (ACTH), Growth Releasing Factor (GRF), Corticosterone, Prolactin, Cortisol, Testosterone, Follicle Stimulating Hormone (FSH), a biomarker related to Gastroenterology such as Gastrine, Lipase, a biomarker related to Infectious Diseases such as Anti-Borrelia, Anti-Rubella, Anti HBs, Anti-HBc, Anti-HBe, Anti-HCV, Anti-HIV I/II and other antibodies to infectious agents as well as specific antigens being part of the infectious agent such as HIV-p24, HBsAg and others, biomarkers related to Inflammation/Immunity such as Immunoglobulins (IgA, IgG, IgM, IgE, IgD and subclasses thereof), Clusterin (Apolipoprotein J), C-Reactive Protein (CRP), CRPhs (ultrasensitive), Procalcitonin (PCT), Heparin Binding Protein (HPB), Calprotectin, Human Neutrophil Lipocalin/Neutrophil Gelatinase-Associated Lipocalin (HNL/NGAL), Endothelin-1, Fibrinogen, Glucose-6-Phosphate Dehydrogenase (G-6-PDH, Monokine Induced by IFNγ (MIG/CXCL9), IFN-alpha, Neopterin, IFNγ (IL-2, IL-4, IL-10)-4-plex, IL-10, IL-10 (IL-2, IL-4, IFNγ)-4-plex, IL-1β, Rantes/CCL5, IL-2 (IL-4, IL-10, IFNγ)-4-plex, IL-4 (IL-2, IL-10, IFNγ)-4-plex, Tumor Growth Factor (TGF-β1), IL-6, Tumor Necrosis Factor (TNFα), IL-8, biomarkers related to Lipid Metabolism such as Apolipoprotein AI (Apo AI), Cholesterol, Apolipoprotein AII (Apo AII), HDL-Cholesterol, Apolipoprotein B-100 (Apo B), LDL-Cholesterol, Apolipoprotein B48 (Apo B48), Lecithin Cholesterol Acyltransferase (LCAT), Apolipoprotein CII (Apo CII), Paraxonase (PON1), Apolipoprotein CIII (Apo CIII), Phosphatidyl Inositol Glycan F (PIGF), Apolipoprotein E (Apo E), Triglycerides, biomarkers related to Nephrology such as Alpha-GST, Beta-2-Microglobulin (serum), Microalbumin, Beta-2-Microglobulin (urine) Cystatin C, Creatinine, biomarkers related to Oncology such as Carbohydrate Antigen 19-9 (CA19-9), Prostate Specific Antigen (PSA), Carcinogenic Embryonic Antigen (CEA), Vascular Endothelial Growth Factor (VEGF), Fibroblast Growth Factor (FGFb), and biomarkers related to Thyroid conditions such as Anti-Thyroid Peroxidase Ab (TPO), Thyroid Stimulating Hormone (TSH), Anti-Thyroglobulin Ab, Total Thyroxin (T4), Free Thyroxin (FT4), Total Triiodothyronin (T3), Free Triiodothyronin (FT3), TSH Receptor Ab, and Thyroglobulin.

The term "tracer substance" is intended to encompass any substance which is either able to bind to an analyte of interest (e.g. a biomarker) or a bead (the term bead is defined below), and display properties that make them quantifiable or identifiable by any suitable technique common in the art of analytical chemistry/biology (i.e. they may be detected optically, magnetically, electrically or by radiation). Properties of particular interest are those which enable optical detection, e.g. the tracer substance may absorb and/or scatter light such as a chromophore, or display luminescent properties such as fluorescence or phosphorescence, or the tracer substance is not directly optically detectable, but able to react with a further substrate to provide a reaction product which is optically detectable. The binding part of the tracer substance which is suitable for binding to the analyte (e.g. a biomarker) of interest, or bead, comprises for instance proteins, nucleic acids, carbohydrates and chelating compounds. Specific binding parts include antibodies, antigens, nucleic acid probes or other bio-specific receptor ligand systems.

Examples of tracer substances suitable for use in the present method include those comprising nanoparticles, preferably metal based nanoparticles, and enzymes. The nanoparticle of a tracer substance is typically 3 to 100 nm in diameter. Preferred nanoparticles include metal based particles such as gold ($\rho=19.3$ g/cm$^3$), silver ($\rho=10.5$ g/cm$^3$), or iron ($\rho=7.9$ g/cm$^3$) colloids and inorganic crystals such as upconversion nanoparticles (UCNPs; $\rho$ typically 4 to 5 g/cm$^3$).

Use of metal based nanoparticles as tracer substances is well known, for a review of gold nanoparticles see for instance S. Zeng et al.; "A review on functionalized gold nanoparticles for biosensing applications". *Plasmonics* 6 (3): 491-506.

For a review of UCNPs suitable for use in the present method see for instance Cheng et al. *Nanoscale*, 2013, 5, 23 and Ang et al. *Nanomedicine*, 2011, 6, 1273.

Use of fluorophores as tracer substances are comprehensively referenced in for instance *The Molecular Probes@ Handbook—A Guide to Fluorescent Probes and Labeling Technologies*, by Life Technologies™.

Other substances which are not optically detectable per se may also be used as tracer substances. For instance, when the present method is used for performing an ELISA-type assay the final analysis of the resulting bead-analyte-tracer substance complex is not depending on a direct optical detection of the tracer substance, but on the reaction product (providing a color or fluorescent or electrochemical signal) from a reaction between an enzyme on the tracer substance and a suitable substrate.

Examples of methods for synthesizing suitable tracer substances are comprehensively disclosed in the prior art, and obtaining tracer substances suitable for the method of the present invention is well within the knowledge of a person skilled in the art of synthetic chemistry or biochemistry.

The term "bead" is intended to encompass any type of solid phase particles or beads, and are preferably spherical micro- or submicro-particles having a diameter of 0.1 to 50 µm, 0.5 to 50 µm, preferably a diameter of 2 µm to 20 µm. These particles may be porous or have a smooth solid surface. They may be compact or have one or more shells surrounding one or more central core material within the beads that might be solid materials, liquids or gases. The beads may be opaque or transparent. Preferably the beads are substantially transparent and made from polymers with a volumetric mass density ($\rho$) slightly above the density of water ($\rho=1.0$ g/cm$^3$). Typically, the beads are made of polystyrene ($\rho=1.05$ g/cm$^3$), polymethylmethacrylate ($\rho=1.18$ g/cm$^3$) or other suitable materials. Further, a bead comprises multiple covalently coupled molecular structures or entities able to bind an analyte of interest. Such molecular structures or entities may for instance be an antibody or fragments thereof, a nucleic acid, an aptamer, a chelating structure and similar. In the present disclosure the beads may in the case of competitive assays also comprise a defined amount of analyte-tracer substance units (i.e. a unit consisting of an analyte bound to a tracer substance). The term "defined amount" is in this regard intended to denote that the beads are standardized to provide a known analytical result or signal. By analyzing the beads, which initially have a defined amount of analyte-tracer substance units, after interaction with a competing analyte from a sample and comparing the analytical result with said known analytical result, the analyte may be determined/measured.

The term "quantifiable bead-analyte complex" is in the present disclosure intended to mean a complex formed by the interaction between a bead and an analyte. Commonly, the complex comprises a bead, an analyte and a tracer substance. A qualitative and/or quantitative analysis of such a complex will provide an indirect qualitative and/or quantitative analysis of the analyte to be determined from a sample. The specific structure of a quantifiable bead-analyte complex will differ according to the type of assay performed. For instance, in a non-competitive assay, the complex will ideally comprise a bead, wherein the bead is only bound to at least one analyte-tracer substance unit, while in a competitive assay, the complex may comprise a bead bound to both an analyte-tracer substance unit and an analyte, originating from the sample, without a tracer substance. Further variants of quantifiable bead-analyte complexes are also possible, only depending on the type of assay.

The term "sandwich complex" is in the present disclosure intended to mean a complex comprising a bead, an analyte and a tracer substance. A "sandwich complex" is typically a quantifiable bead complex, but the term may in connection with competitive assays also denote a bead comprising a defined amount of analyte-tracer substance units as described above.

The terms d, d1, d2 etc. are intended to denote the volumetric mass density of a given liquid medium in $g/cm^3$.

The terms m, m1, m2 etc. are intended to denote the volumetric mass density of a given solid material in $g/cm^3$.

The term "liquid medium" is intended to encompass any liquid suitable for use in the specific assay performed. The suitability of a particular liquid medium in a particular assay is easily appreciated by the skilled person. Further, the required volumetric mass density of any liquid may be altered by additives that are dissolved in or mixed with the liquid. This is true for any type of material involved, like various substances, salts, liquid or gasses, provided they will mix and dissolve properly. The alteration of density is related to concentration and relative density of the substances involved. All dissolvable compounds having a different density than the solvent will affect the density of the solution/liquid. Typically sea water has a higher density (surface 1.025 $g/cm^3$) than pure fresh water (1.00 $g/cm^3$). A variety of substances are used to change the density of aqueous solutions, particularly in the field of density gradient centrifugation. These include substances like sucrose, sucrose polymers, various coated colloids and Cesium Chloride, as well as a variety of Iodine containing substances, such as iodixanol, iohexol, metrizamide and others, that readily dissolves in water in high concentration.

The term "reactant" in the context of the present application is intended as a general term for a component present in the analytical method, such as an analyte, tracer substance or a binding molecular entity on a bead.

The term "dried formulation" refers to reagents, including preparations of beads and nanoparticles that may be incorporated into a device used for running the assay. These dried formulations may be made by vacuum drying or by freeze drying. Freeze dried formulations prepared as uniform spherical aliquots with a size between less than 1 µL to 200 µL. These may be produced in bulk and then dispensed one by one into the analytical device.

The present invention concerns a novel method for transferring or moving beads, or solid phase particles, in the internal fluid circuit of a fluidic or microfluidic chip or cartridge. The method of the present invention may advantageously be combined with an analytical assay, such as the one described in the following.

In the disclosed method of analysis, a very efficient interaction between reactant(s) in a first solution, and reactant(s) attached to the surface of solid phase particles, is combined with a very efficient washing of the solid phase particles by bringing them into suspension using a second solution.

The solid phase particles are micro-sized beads or spherical particles.

The reactants, both in solution and attached to the surface of the solid phase particles will vary according to the type of assay being performed.

In a sandwich type non-competitive immunoassay, the reactants in solution will be an analyte (for instance some type of biomarker present in a biological sample) and a tracer substance (for instance a labeled antibody selective for the specific biomarker). Said reactants may be mixed before interaction with the solid phase particles, i.e. applied simultaneously or as a preformed analyte-tracer substance unit, or applied sequentially (i.e. the analyte is attached to the solid phase particles before a tracer substance is applied). The reactants on the surface of the solid phase particles will be a molecular structure (e.g. an antibody) able to bind the analyte and/or the analyte-tracer substance unit.

In a competitive immunoassay, the reactants in solution may be a mixture of the analyte present in the sample and an amount of analyte-tracer substance units displaced from the bead by sample analytes. The reactants on the surface of the solid phase particles (i.e. beads) will comprise a molecular entity or structure (e.g. an antibody) able to bind the analyte present in the sample, and wherein the molecular structure is originally bonded to an analyte-tracer substance unit.

To obtain an efficient interaction, the solid phase particles are closely packed in a structure, such as a column. This is preferably achieved by having the solid phase particles withheld in a section, or cavity, of a fluid circuit in an assay device (e.g. a fluidic or microfluidic chip). The section or cavity may advantageously be substantially column-shaped, but other shapes or forms are suitable. The solid phase particles are preferably withheld in the cavity by a particle retaining element, such as a filter element, arranged in the section, or cavity, of the fluid circuit. The traps disclosed in WO 2011/081530 A1 are an alternative solution for providing a cavity comprising a particle retaining element not requiring the use of a filter element.

The filter element is designed or selected to have a pore size or slit size that will not allow the solid phase particles to pass through it. The liquid solution is removed from the solid phase particle column or particle suspension by applying a centrifugal force acting from the side of the column opposite the filter element and towards said element. In this manner, the liquid solution is forced through the solid phase particle column and the filter structure.

The flow of liquid through the filter may be controlled using a valve controlling the outlet of liquid passing through the filter. This could alternatively be done by controlling the counter pressure applied to the outlet liquid as of a liquid column immerging substantially parallel to the column-shaped cavity containing the solid phase particles. The liquid may then be removed from the particles by altering the orientation of the assay device (e.g. a fluidic or microfluidic chip) relative to the centrifugal force.

To obtain an efficient washing of the solid phase particles, the particles are suspended by adding a second liquid solution. The second liquid solution has a density which is higher than the volumetric density of the solid phase particles. The solid phase particles will in this liquid, when exposed to centrifugal forces, start unpacking from their column-shaped structure and migrate by floatation towards the surface of the high density liquid being closest to the axis of centrifugation. By this means, the solid phase particles will on their way towards the surface be dispersed in the solution and also separated from any unbound tracer reagents (e.g. unbound tracer substance or unbound analyte-tracer substance units), and other soluble or dispersible components, that were trapped in the column-shaped structure of packed solid phase particles during the interaction of the reactants in solution with the solid phase. The dispersion of the solid phase particles in the second liquid solution as obtained by floatation will hereby allow efficient washing of these particles when the second liquid solution is drained from the column-like cavity by filtration.

The separation between "low density" solid phase particles and other dispersible materials may be further facilitated, when these latter materials include particles with higher density than the second liquid. These particles may be high density nanoparticles such as metal colloids or polymer microparticles with higher density than the second liquid. In this situation, the particles with higher density than the second liquid are pulled away from the axis of centrifugation, while the low density particles move towards the axis of rotation. The degree of separation will depend on the differences in density of the involved components and liquids involved, the size of the particles, the centrifugal force applied and the time of centrifugation.

The packed solid phase particles are thus suspended by altering the density of the solution surrounding the particles. When the density of this solution, i.e. the second liquid solution, is higher than that of the particles themselves, the particles will float, i.e. move in a direction opposite the direction of the applied gravitational or centrifugal force. When centrifugal forces are acting on particles of lower density than the liquid surrounding them, they will gradually migrate to the surface of the solution being closest to the centrifugal center, while components of higher density than the liquid will tend to sediment, i.e. migrate to the volume of the solution being furthest from the centrifugal center. A major advantage obtained by suspending the solid phase particles after having performed the binding step of an assay is that any excess of tracer substance that are trapped or captured in a non-specific manner due to the porous structure, obtained by packing the solid phase particles in a column, is released and thus more easily removed.

By this means, for instance, tracer substances with higher density than the liquid can efficiently be separated from components of lower density than the liquid. The liquid including the higher density components dispersed in the liquid may then be drained out through the filter, while the solid phase particles will be stopped when they reach the filter. Repeated washing steps of the solid phase particles may be performed by repeated re-suspensions and draining steps.

Having tracer substances of a density higher than the solid phase particles is advantageous, but the re-suspension of the solid phase particles packed into a column will also provide a much improved washing step when the tracer substances have an equal or lower volumetric density than the solid phase particles. In the latter case, the tracer substance is still released from the porous structure as discussed above, and thus more easily removed from the solid phase particles when the second liquid solution is drained through the filter element.

This solution provides a simple means for washing off the excess of tracer substance.

An additional advantage of using solid phase particles or beads in a lab-on-a-chip device (i.e. microfluidic chip, processing cartridge or similar) is that beads in suspension may, throughout the assay, be transferred to different position/locations within the device. This may include fluidic transfer of the particles to cavities or sections of a fluid circuit that are not previously contaminated with the tracer substance and/or to cavities that are designed specifically for optimized functionality of the individual steps. This may for example allow for first having the beads in a cavity optimized for storage, then transfer the beads to a cavity optimized for fast interaction (i.e. a column shaped structure), then transfer the beads to a cavity optimized for washing, further to a cavity optimized for readout and finally transfer to a cavity for waste storage.

As described, the device used for analyzing the sample may be a microfluidic chip or cartridge specifically designed for microfluidic processing of both the samples and the reagents according to a specific procedure. These cartridges are usually operated by an instrument that will process the fluids within the cartridges by pumps, valve, centrifugal force or other physical means. In particular, the present invention relates to assay systems that are operated within a microfluidic chip by centrifugal force or gravity.

In an inventive concept, the present application also discloses an efficient method for separating beads, or solid phase particles, of different densities. This concept allows for the analysis of multiple analytes at the same time, followed by easy separation of the different resulting quantifiable bead complexes. The concept is further described below.

The present invention is a method, suitable for use in e.g. an analytical method as disclosed herein, by which beads, or solid phase particles, may be efficiently transferred from one cavity or section to another by using a liquid with higher density than the beads by decanting, thus transferring, the beads floating in the upper fraction of the liquid, i.e. the beads that have migrated (or floated) in a direction towards the axis of rotation generating the centrifugal force, into another cavity. The present invention is further described below.

Both the present invention and the inventive concept may advantageously be combined with an analytical method, e.g. as described below, but are not in any way limited to such use.

Analytical Method Suitable for Use with the Transfer Method

A schematic representation of an analytical method is shown in FIGS. 1a-k. The method is intended for analyzing a sample with respect to one or more analytes of interest. The method is suitable for any type of sample that may be dissolved in a liquid, and also for detecting/quantifying any type of compound or substance in said sample for which an assay for performing such an analysis may be provided.

In the following, the sample is assumed to be a biological sample, and the target compounds or substances are preferably biomarkers, and may be proteins (antigens, enzymes, antibodies), nucleic acids, drugs, hormones, nutrients, metabolites, microorganisms, cells or any such molecule or assembly of molecules that could be measured in an assay including one or more selective binders. The method is based on the well known principle of reacting a biomarker with a solid phase particle (i.e. micro-sized beads, spherical particles etc.), wherein the solid phase particle comprises a molecular structure or entity able to bind with the biomarker.

Suitable molecular entities are for example antibodies if the biomarker is an antigen. In addition to the solid phase particles and the biomarker, a tracer substance must be present. The tracer substance features a molecular entity able to bind the biomarker.

The solid phase particles or beads are as defined above.

The tracer substance(s) are as defined above.

The first steps of a typical heterogeneous immunoassay consists of interacting, contacting, incubating, flushing or mixing, the biological sample, comprising the biomarker to be quantified or identified, with beads and/or tracer substances in a first liquid medium, see FIGS. 1a-e. A sandwich type configuration is in this case established where the target biomarker is working as the linker between the solid phase particle and the tracer substance. These interactions could be performed sequentially in both orders or with all the involved reactants applied together. Preferably, there is established a fixed stoichiometric ratio between biomarker and tracer substance of 1:1 in these "sandwich complexes". In a non-competitive assay, both the beads and the tracer substances are able to bind the biomarker. The tracer substances and the solid phase particles may carry several biomarker specific receptors and may hence bind to several biomarker molecules. Usually, however, the assays are designed to contain a large excess of tracer substances relative to the biomarker. Statistically each biomarker molecule will thereby bind only to one tracer substance. Each microspheric bead does, however, expose a very large surface and may bind numerous target biomarkers and subsequent tracer substances.

In this specific simplified embodiment as shown for the illustration of the principle, the assay is performed in a W-shaped cavity, fluid circuit or test tube arrangement 1. The cavity 1 comprises a first outlet 2 and a second outlet 3, an inlet 4 and a first filter element 5 and a second filter element 6. The first filter element 5 arranged between the inlet 4 and the first outlet 2. A section arranged between the inlet and the first filter element forms a column structure 7. The section, or cavity, may be considered to comprise an outlet 16. The arrow G denotes the direction of an applied centrifugal force (or the gravitational force, although the use of gravity only would provide a significantly slower assay) in relation to the cavity or test tube. The cavity 1 may be part of a fluid circuit in a fluidic or microfluidic chip, for instance a microfluidic chip as disclosed in the prior art described in the background section of the present disclosure. In that case the cavity may be considered as being arranged in a plane being perpendicular to an axis of rotation external to the microfluidic chip. Thus, the required centrifugal force G is obtained by rotation of the microfluidic chip around said axis, and the direction of the centrifugal force in relation to the cavity in the microfluidic chip may be altered by rotating the microfluidic chip itself.

Figure 1B:
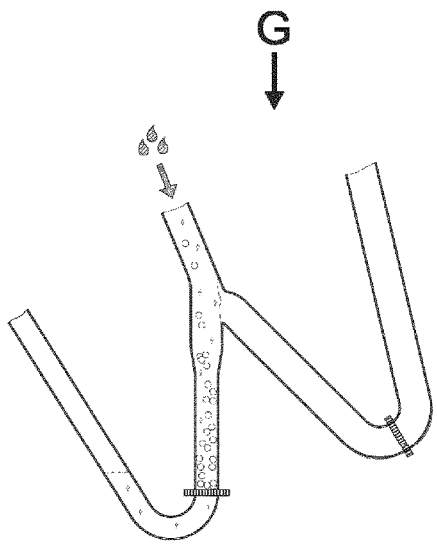
Figure 1C:
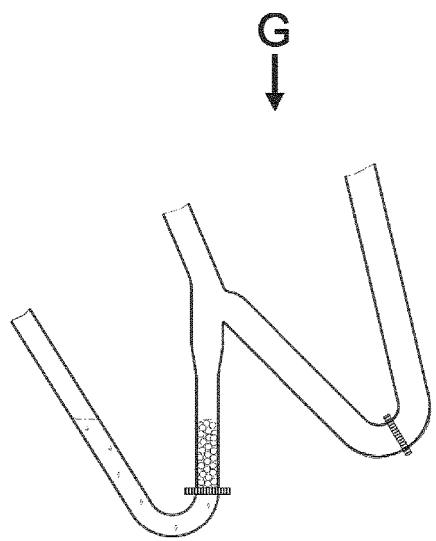
Figure 1G:
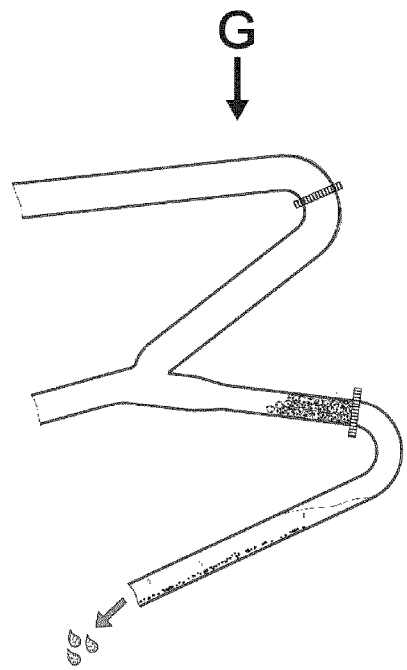
Figure 1H:
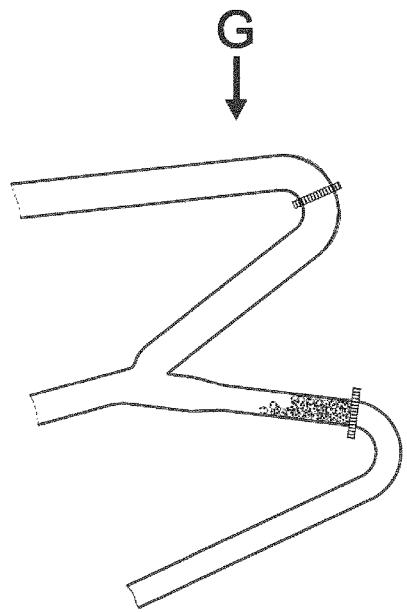
Figure 1I:
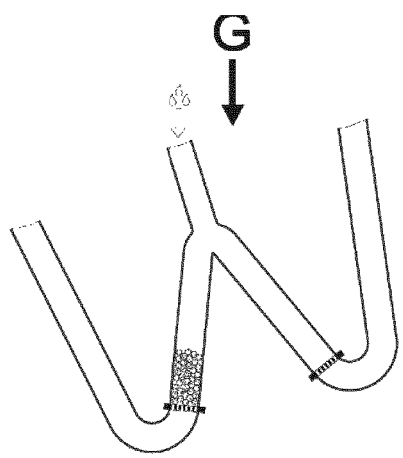
Figure 1J:
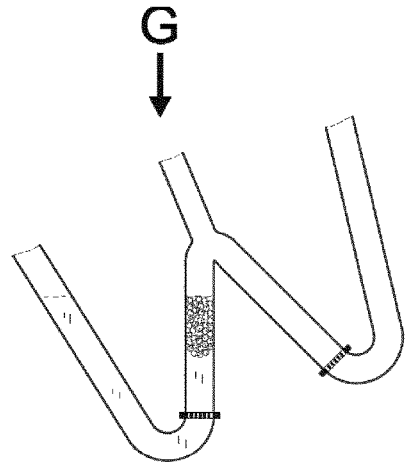
Figure 1K:
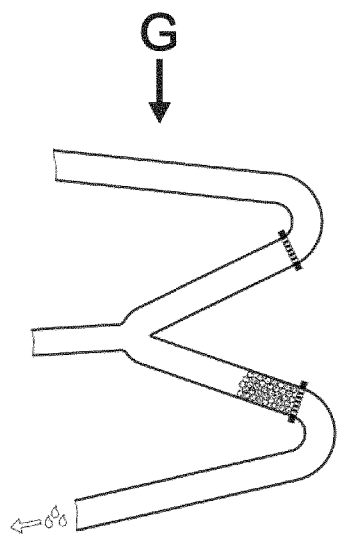
Figure 1L:
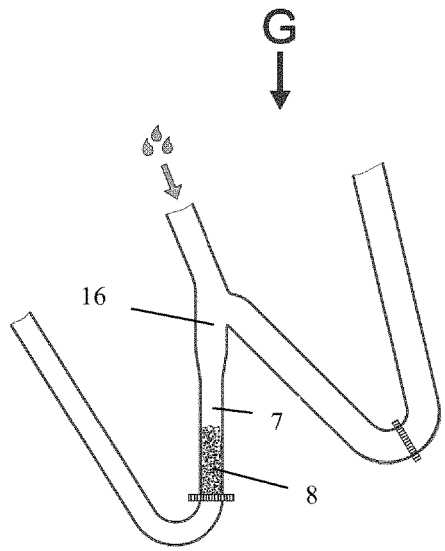
FIGS. 1l-1p are schematic drawings showing the present invention, i.e. a method for moving beads in a microfluidic circuit. The present invention may advantageously be combined with the analytical methods described herein.
Figure 1M:
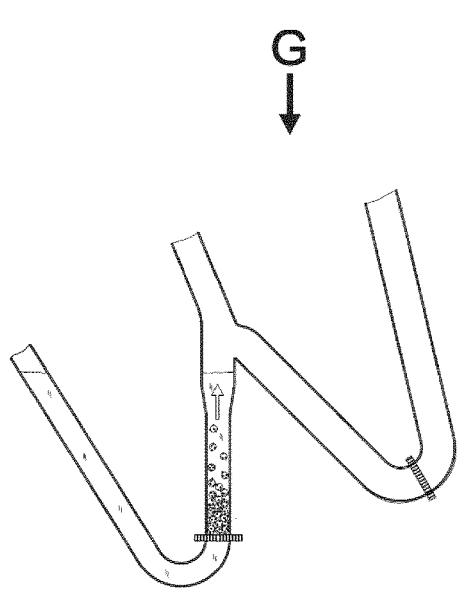
Figure 1N:
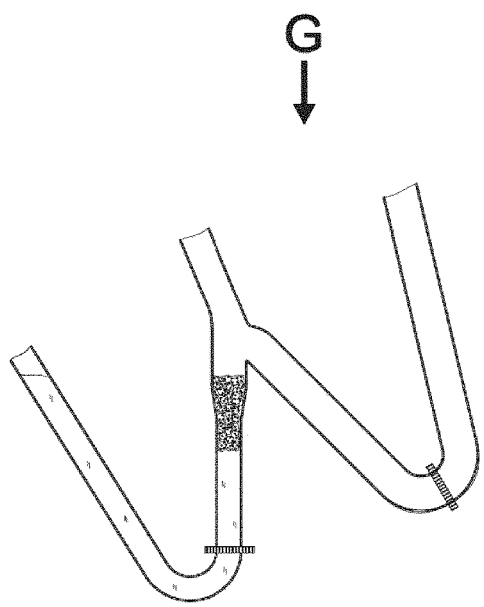
Figure 1O:
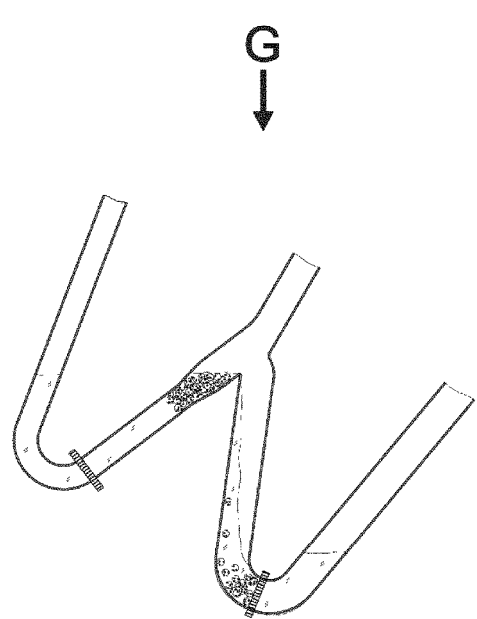
Figure 1P:
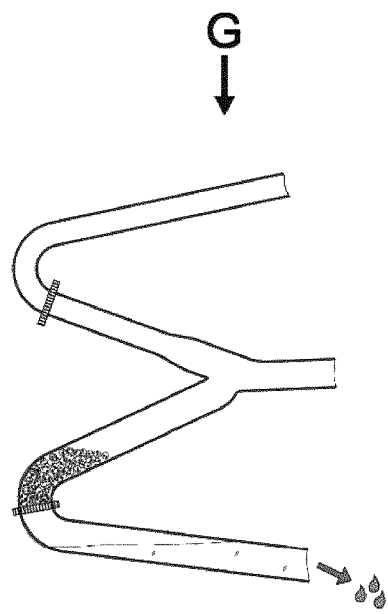

In FIGS. 1a-1p, the various parts of the W-shaped cavity (or section of a fluid circuit) are illustrated as being in one plane, for example arranged at the same horizontal level within a fluidic chip. However, in many instances parts of the W-shaped cavity may advantageously be arranged at different horizontal levels connected by substantially vertically directed channels. As illustrated in FIG. 3, sections of the W-shaped cavity or fluidic circuit may be arranged in two or more levels with transversal channels 17, 18 and 19 connecting the lateral channels as illustrated within L1 and L2. Filters (5 Detail A) and/or other functional elements including particle traps are preferably placed within or based on one or more such transversal channels (6 Detail B).

The specific assay illustrated by FIGS. 1a-e is a non-competitive assay. In such an assay the sequence in which the various components of the assay are interacted, contacted, or mixed, may be chosen arbitrarily since both beads 8 and tracer substances 9 (see FIG. 1d) are provided in a large excess, and they will not react with each other without the presence of an intermediate biomarker. Further, the mixing, interacting or contacting (i.e. the binding step) may advantageously comprise passing the above-mentioned first liquid medium through a plug, or column, formed by the beads 8 to ensure that the reaction between the beads, the tracer substances 9 and the biomarker is as complete as possible. The plug or column is obtained by having the beads packed in a column-shaped cavity 7 or volume. The column-shaped cavity 7 may preferably be a part of a fluid circuit in a lab-on-a-chip device (i.e. a fluid circuit in a microfluidic chip or processing cartridge).

In FIGS. 1a and 1b, beads suspended in a liquid medium are introduced through the inlet 4. The liquid medium has a density lower than the density of the beads. The density of the beads is denoted m1 g/m$^3$. Due to the centrifugal force G, the beads will pack into a column-shaped structure delimited by the column-shaped cavity 7 and the first filter element 5, see FIG. 1c. The beads are withheld in the column-shaped cavity due to the first filter element 5 arranged at one end of said cavity. The filter element may comprise a filter, grid, sieve, narrow slit(s) or similar, and is able to prevent the beads from passing through it.

In a next step, see. FIG. 1d, tracer substance 9 suspended in a liquid medium comprising a biomarker is introduced through the inlet 4. In this specific embodiment, the sample comprising the biomarker has been allowed to interact with the tracer substance before interaction with the beads, and the sample may thus form a part of the liquid medium in which the tracer substance is suspended. The combined liquid medium obtained from the liquid medium suspending the beads, and the liquid medium suspending the tracer substance, has a density lower than the beads. The combined liquid medium is denoted the first liquid medium, and the density of said liquid medium is denoted d1 g/cm$^3$.

The first liquid medium comprising tracer substance and biomarker, as well as complexes formed by the interaction of tracer substance and biomarker, is passed through the packed beads. When passing the first liquid medium through the packed beads, "sandwich complexes" comprising a bead, a biomarker and a tracer substance are formed. The filter element 5 is such that tracer substance 9, and complexes formed by the interaction of tracer substance and biomarker, may pass through, see FIG. 1d. The first liquid medium is passed through the column and led out of the W-shaped cavity 1 or test tube by changing the direction of the applied centrifugal force G, see FIGS. 1f-h. In alternative embodiments, the first liquid medium may for instance be led out of the cavity by use of a valve situated below the first filter element.

The sequence of interaction between the beads 8, tracer substance 9 and biomarker depends on which solution is most appropriate, or suitable, in a particular case. Thus, the sample comprising the biomarker may be part of the liquid medium in which the tracer substance 9 is suspended, or a part of the liquid medium in which the beads 8 are suspended.

The interaction between beads, tracer substance and biomarker may not be complete after a single pass of the first liquid medium through the column of packed beads. Advantageously, the first liquid medium which may comprise unreacted tracer substance, biomarker and complexes formed by the interaction of tracer substance and biomarker (i.e. analyte-tracer substance units) is passed through the packed beads repeatedly by reintroduction into the inlet 4. Such reintroduction may for instance be achieved by having a loop structure (e.g. a fluid circuit formed as a loop) connecting the first outlet 2 with the inlet 4. The latter solution is especially advantageous when the W-shaped cavity is part of a fluid circuit in a lab-on-a-chip device. After reintroduction the steps according to FIGS. 1*e-h* may be repeated.

Depending on the assay design and the concentration of the biomarker in the sample, each of the beads may carry from none to many thousands of biomarker-tracer substance complexes. As the volume of each bead in a preferred embodiment is substantially larger than the volume of a biomarker-tracer substance complex, the binding of numerous biomarker-tracer substance complexes per bead will not substantially affect the volumetric mass density of the beads. In a typical example the volume of a spherical 5 μm (diameter) bead is close to 2 million times the volume of a 40 nm tracer substance.

The interaction between beads, tracer substance and biomarker provides a column of packed beads comprising "sandwich complexes" (i.e. quantifiable bead complexes) and unreacted tracer substance. The density of the "sandwich complexes" is denoted as m2 g/cm$^3$. During the interaction, some of the unreacted tracer substance 9 is trapped or captured in a non-specific manner due to the porous structure formed by the packed beads. To obtain a sensitive and reproducible analytical result as much as possible of the unreacted tracer substance must be separated from the beads and "sandwich complexes". In the prior art, separation of unreacted tracer substance is performed by repeated washings by passing a washing liquid through the column of packed beads. However, as discussed above, such washing will not remove all the trapped unreacted tracer substance, or require an excessive and time consuming number of repeated washings.

To improve, or even allow for, the separation of the unreacted tracer substance from the beads and "sandwich complexes", a second liquid medium is added to the packed beads, see FIG. 1*i*. The second liquid medium has a density of d2 g/cm$^3$, wherein d2>m1 and m2. It should be noted that when used in an alternative analytical system, wherein the first liquid medium is removed by decanting (i.e. instead of by passing the first liquid medium through a filter element), the density of the combination of the small fraction of the first liquid medium and the second liquid medium may be denoted d2'. However, the numerical value of d2' will be approximately equal to d2, i.e. d2'>m1 and m2 due to the high ratio between the volume of the second and first liquid medium.

An essential feature of the present method is that the second liquid medium has a density which is higher than the beads and the "sandwich complexes". The addition of the second liquid medium will then ensure that the column of packed beads disintegrate, such that the close interaction between the beads is disrupted. When the close interaction between the beads is disrupted, the trapped/captured unreacted tracer substance is released into the second liquid medium. Due to their lower density relative to the density of the second liquid medium, the beads and "sandwich complexes" will move against the direction of the applied centrifugal force G, away from the first filter element 5, see FIG. 1*j*. To remove unreacted tracer substance previously trapped/captured between the packed beads, the second liquid medium is led out of the W-shaped cavity or test tube through the first outlet 2 by changing the direction of the applied centrifugal force G, see FIG. 1*k*. In alternative embodiments, the second liquid medium may for instance be led out of the cavity by use of a valve situated below the first filter element 5.

The most important effect obtained by using a first and a second liquid medium of different densities is that the beads will "sediment" in the first liquid medium, d1<m1 while they will "float" in the second liquid medium, d2>m1. The terms "sediment" and "float" is used to describe the position of the beads in the liquid medium in relation to an applied centrifugal force G, i.e. when the beads "float" they have migrated in a direction opposite the direction of the applied centrifugal force, and vice versa for the term "sediment".

If the remaining amount of unreacted tracer substance is too high after removal of the second liquid medium, the steps of adding and removing a second liquid medium, according to FIGS. 1*i-k* (i.e. washing steps), may be repeated a required number of times using fresh aliquots of the second liquid medium.

As shown in this particular analytical method, the tracer substances may advantageously have a volumetric mass density of n g/cm$^3$, wherein n>m1, m2 and d2. Such a density will ensure that the excess of tracer substance will "sediment" when the second liquid medium is supplied to the beads, and further facilitate the separation of the tracer substance from the beads and "sandwich complexes". This may be particularly advantageous in an alternative embodiment, i.e. an embodiment featuring the transfer method according to the present invention, wherein the beads are moved from the column-shaped cavity by decanting as mentioned above.

However, the tracer substance is not required to have a specific density. Merely the fact that the column of packed beads disintegrates, such that the close interaction between the beads is disrupted, will ensure that an improved removal of the excess tracer substance is achieved when the second liquid medium is removed. In addition to the volumetric mass density, other properties of the tracer substances may decide how they behave in the second liquid medium. For example, if the tracer substances are associated with or comprise nanoparticles, they will tend to stay suspended in a liquid medium over an extended period of time even if their volumetric mass density is lower than the density of the second liquid medium. Other properties or features which will influence the behavior of the tracer substances include their solubility in the liquid medium involved or the presence of any applied forces (i.e. magnetic, electric) that may keep them separated from the floating beads.

As described above the mixture of beads, tracer substance and "sandwich complexes" in the second liquid medium is subjected to a centrifugal force having a first direction. The beads including the "sandwich complexes" (i.e. quantifiable bead complexes) have a volumetric mass density (m1 and m2) that is less than that of the second liquid (d2), and will "float" (i.e. move towards the liquid surface of the second liquid medium being closest to the rotational axis of a centrifugal system), while the excess of unbound tracer substance, depending on its properties such as density n, size, solubility etc. as discussed above, will either "sediment", i.e. move away from the axis of rotation creating the centrifugal force, or stay suspended at least for a time period being sufficient to separate the second liquid medium, and hence the suspended tracer substance, from the beads and "sandwich complexes".

After removal of the unreacted tracer substance the biomarker may be quantified, or identified, in situ (i.e. in the column-shaped cavity 7) by analyzing the multiple "sandwich complexes".

In alternative analytical methods the beads and "sandwich complexes" are transported to a different site or cavity for analysis. When the analytical method disclosed herein is used in a lab-on-a-chip device comprising a microfluidic chip having an internal fluid circuit through which various reactants, including beads, and a sample containing at least one analyte may be moved by use of centrifugal force, the beads comprising the "sandwich complexes" may for instance be transported to a fluid circuit or cavity specifically designed for the analysis of such beads.

In this specific analytical method, the beads including "sandwich complexes" are transferred from section or cavity 7 to a second column-shaped cavity 10 by use of the transfer method according to the present invention. The transfer is achieved by adding a further aliquot of the second liquid medium, or a different liquid medium having the same or higher density as the second liquid medium, to the beads, see FIGS. 1*l-m*. The aliquot is preferably larger than the amount used in the washing steps of FIGS. 1*i-k*, such that the beads may migrate closer to the inlet 4 (or outlet 16, see FIG. 1*l*) of the cavity 7. A fraction of the second liquid medium being closest to the axis of centrifugation (or the inlet 4 or the outlet 16) containing all the beads, including the "sandwich complexes", is transferred into the second column-shaped cavity 10 by decanting, see FIG. 1*o*. The decanting is achieved by a slight change of the direction of the centrifugal force G in relation to the first column-shaped cavity. The second column-shaped cavity 10 is optimally designed for the next preferred action in the assay, i.e. the second cavity may be designed for more extensive washing and/or for quantifying the "sandwich complexes".

In this specific analytical method, the cavity 7, within which the beads are packed, is shown and described as being column-shaped. However, in other analytical methods the cavity may have any shape or form as long as it provides for a packed structure of beads allowing a close interaction between the reactants, and a subsequent dispersal of the packed structure in a liquid medium.

Separating Beads of Different Density in a Fluid Circuit

In the analytical method described by FIGS. 1*a-k*, the method is shown as analyzing one analyte at a time. However, the method is not restricted to analyzing only one analyte at a time.

By using multiple types of beads of different densities, each type selective for a different analyte, and respective complementary tracer substances in the interaction with a sample containing multiple types of analytes, multiple types of "sandwich complexes", corresponding to the multiple types of analytes, may be obtained at the same time. The multiple types of "sandwich complexes" may be analyzed at the same time or sequentially. After a binding or interaction step as described above, a column of packed beads would comprise multiple types of beads and corresponding "sandwich complexes" representing the various analytes to be analyzed. In some instances, the multiple types of "sandwich complexes" may be analyzed without separation from each other. However, to obtain a desired level of sensitivity and reproducibility, separation of the multiple types of "sandwich complexes" may be required.

The present disclosure provides an inventive concept for achieving a separation of multiple types of beads/solid phase materials, including "sandwich complexes" as described throughout the description. The concept is not depending on, nor is it an essential part of, the specific analytical method described above. The concept is especially advantageous for use in a lab-on-a-chip device, such as a microfluidic chip comprising an internal fluid circuit through which various reactants, including beads, and a sample containing at least one analyte may be moved by use of centrifugal force.

Figure 2A:
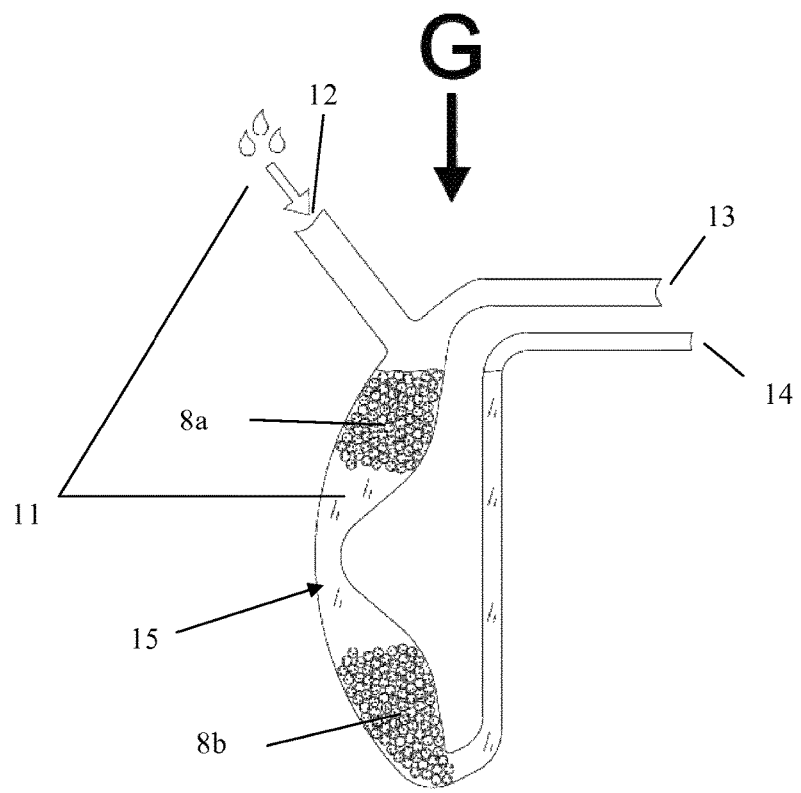
FIGS. 2a-2b are schematic drawings showing an inventive concept for separating beads of different densities in a fluid circuit.
Figure 2B:
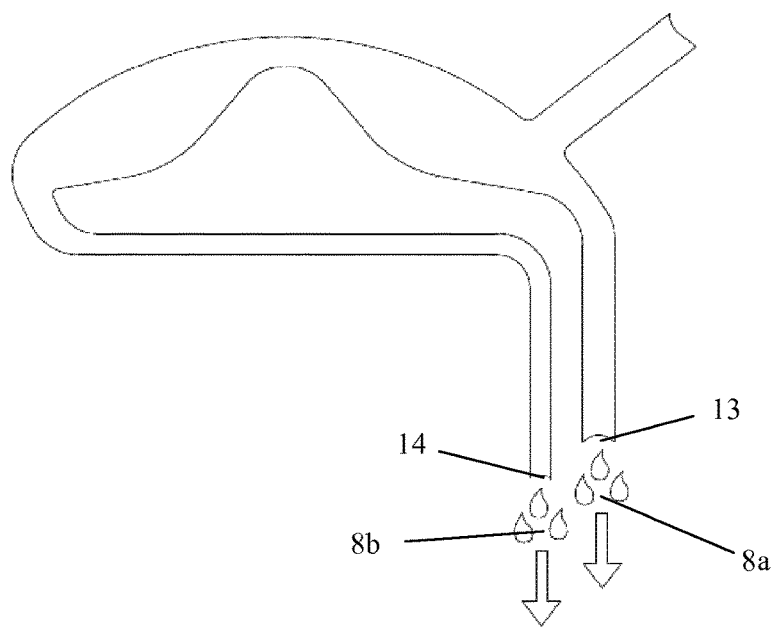

An embodiment of the inventive concept is illustrated in FIGS. 2*a* and 2*b*. A cavity 15 suitable for separating beads having different densities is shown in FIGS. 2*a* and 2*b*. The cavity comprises an inlet 12, a first outlet 13 and a second outlet 14. In this particular case the cavity is provided with a first set of beads 8*a* having a density m1 and a second set of beads 8*b* having a density m2. A liquid medium 11 having a density d3, m1<d3<m2, is then added to the beads in the cavity. A centrifugal force G causes the first set of beads 8*a* to migrate (or float) in the direction of the first outlet 13, while the second set of beads 8*b* migrates (or sediments) towards the second outlet 14. By changing the direction of the centrifugal force, i.e. the orientation of the cavity in relation to the centrifugal force, the first set of beads 8*a* and parts of the liquid medium 11 is transferred through the first outlet 13, whereas the second set of beads 8*b* and parts of the liquid medium 11 is transferred through the second outlet 14.

The inventive concept is also applicable to other cavity designs such as the one already shown in FIG. 1*a*. In a cavity as shown in FIG. 1*a*, a liquid medium having a density d3 (as described in connection with FIGS. 2*a* and 2*b*) may first be used to separate two sets of beads (similar to the action in FIG. 2*a*). By changing the direction of the applied centrifugal force G after the two sets of beads are separated, the first set of beads may be decanted from the column-shaped cavity 7 (similar to the decanting of beads in FIG. 10) by using the transfer method of the present invention. A first and second set of beads may thus be separated. By addition of a further liquid medium having a density d4, d4>m2, to the column-shaped cavity 7, the second set of beads may subsequently be decanted from said cavity in the same manner used for the first set of beads, i.e. by a further use of the transfer method according to the invention.

The inventive concept of separating beads of different densities is not restricted to only two sets of beads having different densities, but may be used to separate any number of sets of beads as long as they have different densities allowing for separation by applying a liquid medium of suitable density. For instance in the case of a cavity as shown in FIG. 1*a*, four sets of beads having densities m1, m2, m3 and m4, respectively, may be separated sequentially by first adding a liquid medium having a density d3, m4<d3<m3, m2, m1, decanting of the beads having a density m4 (similar to the beads in FIG. 1*o*), filtering off the remaining liquid medium having a density d3 and adding a further liquid medium having a density d4, m3<d4<m2, m1 (alternatively, the remaining liquid medium having a density d3 is not filtered off, but its density is increased to d4 by addition of a density increasing additive such as a further high density liquid), decanting of the beads having a density m3 etc.

A further option is to separate the beads into two combined sets of beads, wherein the first combined set comprises the beads of density m1 and m2, while the other combined set comprises the beads of density m3 and m4. This may be obtained by first adding a liquid medium having a density d4, m4, m3<d4<m2, m1, and decanting of the beads having a density m4 and m3. Each combined set of beads may then, for instance, be transferred to a cavity as shown in FIG. 2*a* for further separation. When the first concept is used in an analytical method, for instance the method described above, a set of beads may also comprise "sandwich complexes" to be analyzed.

Embodiments may include the following:

A method of separating beads in a microfluidic chip comprising an internal fluid circuit through which various reactants, including beads and a sample containing at least one analyte, may be moved by use of centrifugal force, the method comprising the steps of:

provided at least a first set of beads having a density m1 and a second set of beads having a density m2 in a cavity of the fluid circuit, the cavity comprising at least a first outlet;

providing a first liquid medium to the cavity, the liquid medium having a density d3, such that m1<d3<m2; and applying a centrifugal force such that the first set of beads and the second set of beads migrates in opposite directions within the cavity.

In one embodiment of the method of separating beads in a microfluidic chip, the first set of beads migrates towards the first outlet.

In one embodiment of the method of separating beads in a microfluidic chip, the method comprises the step of:

transferring the first set of beads out of the cavity by changing the direction of the centrifugal force, while the second set of beads remain in said cavity, preferably such that the first set of beads are decanted through the first outlet.

In one embodiment of the method of separating beads in a microfluidic chip, the cavity comprises a second outlet, and the method comprises the step of:

changing the direction of the centrifugal force such that the first set of beads is transferred through the first outlet and the second set of beads is transferred through the second outlet.

Transferring Beads in a Fluid Circuit

In relation to transportation of beads, the present disclosure describes an invention which is not depending on, nor is it an essential part of, the analytical method described above. An embodiment of the present invention is disclosed in FIG. 1l-p. The invention solves a problem which is especially relevant in relation to lab-on-a-chip devices, such as microfluidic chips, wherein beads are to be transported through fluid circuits by use of centrifugal force. In the prior art, the transportation of beads is always performed in the same direction as the centrifugal force, and the options available for design of the fluid circuits are thus restricted. The present invention allows for the transportation of beads in a direction opposite an applied centrifugal force by adding a liquid medium having a density d2, to beads having a density equal to, or lower than, m1, wherein d2>m1.

Although the present invention is illustrated by reference to the column-shaped cavity 7 of FIGS. 1l-1p, the invention is equally suitable for cavities having a wide variety of shape and form. A further example of a suitable cavity 15 is shown in FIGS. 2a and 2b. As disclosed in the description of the inventive concept above, the first set of beads 8a is caused to migrate (or float) in the direction of the first outlet 13, the direction being opposite that of the applied centrifugal force G.

The invention claimed is:

1. A method of transferring beads in a fluidic chip comprising an internal fluid circuit through which various reactants, in which at least one of the reactants are beads, may be moved by use of centrifugal force, the method comprising:

providing beads having a density equal to, or lower than, m1 in a section of the fluid circuit, the section comprising at least a first outlet;

providing a first liquid medium to the section, the liquid medium having a density d2, such that d2>m1; and applying a centrifugal force to the fluidic chip such that the beads migrate in an opposite direction of the centrifugal force.

2. The method of claim 1, wherein the beads migrate towards the first outlet.

3. The method of claim 1, comprising:

transferring the beads out of the section by changing a direction of the centrifugal force such that the beads are decanted through the first outlet.

4. The method of claim 1, wherein the fluidic chip is arranged in a centrifuge capable of providing the centrifugal force.

5. The method of claim 1, wherein the fluidic chip is a microfluidic chip.

6. The method of claim 1, wherein a direction of the centrifugal force relative to the internal fluid circuit may be varied in at least two separate directions.

7. The method of claim 1, wherein the reactants includes a sample containing one or more analytes.

* * * * *